(12) United States Patent
Baril et al.

(10) Patent No.: US 11,051,828 B2
(45) Date of Patent: Jul. 6, 2021

(54) ROTATION KNOB ASSEMBLIES AND SURGICAL INSTRUMENTS INCLUDING SAME

(71) Applicant: Covidien LP, Mansfield, MA (US)

(72) Inventors: Jacob C. Baril, Norwalk, CT (US); Brian J. Creston, West Haven, CT (US); Thomas A. Zammataro, Hamden, CT (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 140 days.

(21) Appl. No.: 16/433,017

(22) Filed: Jun. 6, 2019

(65) Prior Publication Data

US 2020/0046367 A1     Feb. 13, 2020

Related U.S. Application Data

(60) Provisional application No. 62/717,983, filed on Aug. 13, 2018.

(51) Int. Cl.
*A61B 17/128*     (2006.01)
*A61B 17/00*     (2006.01)
*A61B 17/29*     (2006.01)

(52) U.S. Cl.
CPC .. *A61B 17/1285* (2013.01); *A61B 2017/0046* (2013.01); *A61B 2017/00407* (2013.01)

(58) Field of Classification Search
CPC .... A61B 2017/0046; A61B 2017/2929; A61B 2017/00464; A61B 2017/2927;
(Continued)

(56) References Cited

U.S. PATENT DOCUMENTS 3,120,230 A    2/1964   Skold
3,363,628 A    1/1968   Wood
(Continued)

FOREIGN PATENT DOCUMENTS

AU    2013254887 A1   11/2013
CA    1163889 A     3/1984
(Continued)

OTHER PUBLICATIONS

International Search Report corresponding to Int'l Patent Appln. PCT/US2018/050316 dated Dec. 31, 2018.
(Continued)

*Primary Examiner* — Majid Jamialahmadi

(57) ABSTRACT

A rotation knob assembly for a surgical instrument includes an outer knob, an intermediate collar, an inner sleeve, a retaining clip, and screws. The outer knob defines a knob lumen extending longitudinally therethrough and longitudinal apertures disposed in radially spaced relation relative to a distal lumen portion of the knob lumen. The intermediate collar is disposed within the knob lumen and defines a collar lumen extending longitudinally therethrough. The inner sleeve is disposed within the knob lumen and extends through the collar lumen. The retaining clip includes a curved body disposed within an annular groove defined in an exterior surface the inner sleeve and prongs disposed at opposed ends of the curved body that are aligned with the longitudinal apertures of the outer knob. The screws extend through the prongs and into the longitudinal apertures to secure the outer knob and the inner sleeve with one another.

20 Claims, 6 Drawing Sheets

(58) Field of Classification Search
CPC .. A61B 2017/2909; A61B 2017/00407; A61B 17/128; A61B 17/068; A61B 17/1285
See application file for complete search history.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |

(56) References Cited

U.S. PATENT DOCUMENTS

| | | |
|---|---|---|
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |

(56) References Cited

U.S. PATENT DOCUMENTS

| | | |
|---|---|---|
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |

(56) References Cited

U.S. PATENT DOCUMENTS

| | | |
|---|---|---|
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |

(56) References Cited

U.S. PATENT DOCUMENTS

| | | |
|---|---|---|
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartournbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |

(56) References Cited

U.S. PATENT DOCUMENTS

| | | |
|---|---|---|
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0066303 A1* | 3/2013 | Hart ............... A61B 17/29 606/1 |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0296236 A1 | 10/2016 | Whitfield et al. |
| 2016/0338695 A1 | 11/2016 | Hartournbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |

(56) References Cited

U.S. PATENT DOCUMENTS

| | | |
|---|---|---|
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czemik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 103251441 A | 8/2013 |
| CN | 104605911 B | 2/2017 |
| DE | 20 2005 001664 U1 | 5/2005 |
| DE | 202007003398 U1 | 6/2007 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| EP | 3132756 A1 | 2/2017 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017059587 A1 | 4/2017 |
| WO | 2017084000 A1 | 5/2017 |
| WO | 2017124217 A1 | 7/2017 |
| WO | 2017146138 A1 | 8/2017 |
| WO | 2018035796 A1 | 3/2018 |

OTHER PUBLICATIONS

International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.

(56) References Cited

OTHER PUBLICATIONS

European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).

(56) References Cited

OTHER PUBLICATIONS

The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
Extended European Search Report dated Dec. 10, 2019 corresponding to counterpart Patent Application EP 19191226.0.

\* cited by examiner

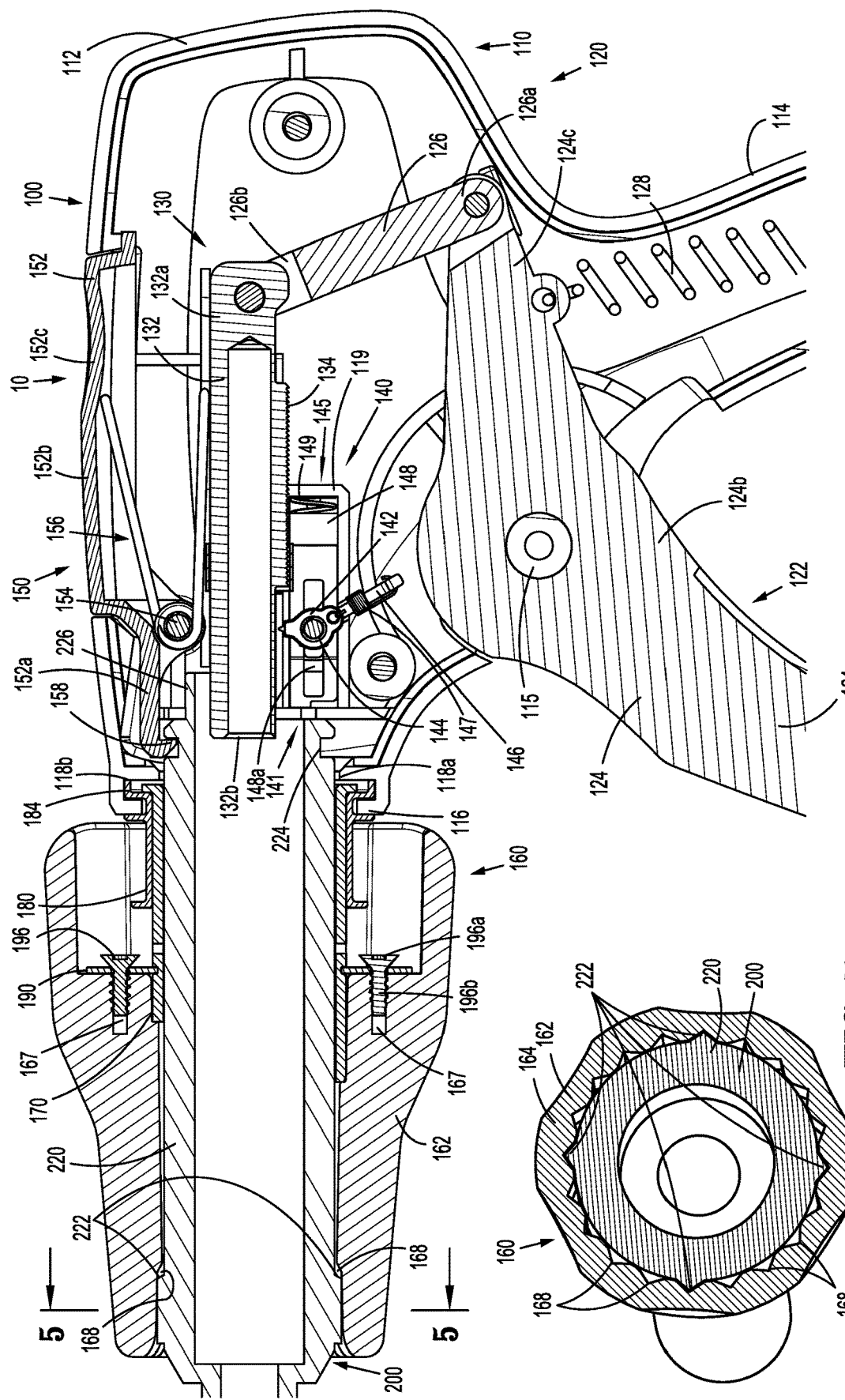

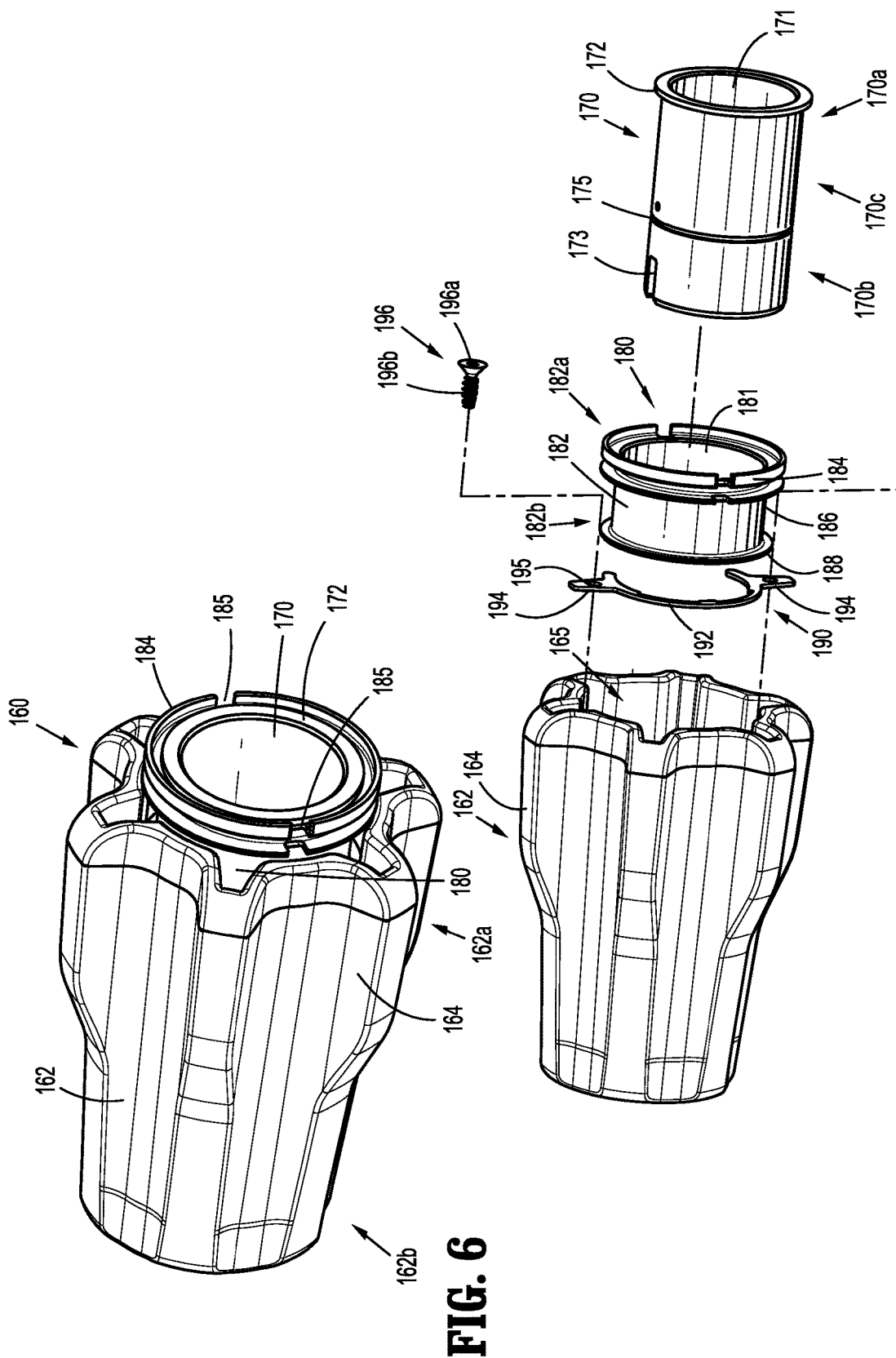

ROTATION KNOB ASSEMBLIES AND SURGICAL INSTRUMENTS INCLUDING SAME

CROSS-REFERENCE TO RELATED APPLICATION

This application claims the benefit of and priority to U.S. Provisional Patent Application No. 62/717,983 filed Aug. 13, 2018, the entire disclosure of which is incorporated by reference herein.

BACKGROUND

Technical Field

The present disclosure relates to rotation knob assemblies for surgical instruments. More particularly, the present disclosure relates to rotation knob assemblies for handle assemblies of endoscopic surgical instruments.

Description of Related Art

Surgical instruments, such as surgical staplers and surgical clip appliers, are known in the art and are used for a number of distinct and useful surgical procedures. In the case of laparoscopic surgical procedures, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into a patient's body through an entrance incision to provide an access port. The access port allows a surgeon to insert a number of different surgical instruments therethrough using a trocar for performing surgical procedures far removed from the incision.

To facilitate orienting an end effector of a surgical instrument relative to the target tissue without rotating an entire handle assembly of the surgical instrument, an endoscopic portion of the surgical instrument is rotatably coupled to the handle assembly by a rotation knob assembly. The rotation knob assembly facilitates rotation of the end effector about a longitudinal axis of the endoscopic portion relative to the handle assembly.

SUMMARY

A rotation knob assembly for a surgical instrument in accordance with aspects of the present disclosure includes an outer knob, an intermediate collar, an inner sleeve, a retaining clip, and screws. The outer knob defines a knob lumen extending longitudinally therethrough and longitudinal apertures disposed in radially spaced relation relative to a distal lumen portion of the knob lumen. The intermediate collar is disposed within the knob lumen and defines a collar lumen extending longitudinally therethrough. The inner sleeve is disposed within the knob lumen and extends through the collar lumen. The inner sleeve includes an annular groove defined in an exterior surface thereof. The retaining clip includes a curved body and prongs disposed at opposed ends of the curved body. The curved body is disposed within the annular groove of the inner sleeve and the prongs are aligned with the longitudinal apertures of the outer knob. The screws extend through the prongs of the retaining clip and into the longitudinal apertures of the outer knob to secure the outer knob and the inner sleeve with one another such that the outer knob and the inner sleeve are together rotatable relative to the intermediate collar.

In aspects, the knob lumen of the outer knob includes a proximal lumen portion having a diameter greater than a diameter of the distal lumen portion of the knob lumen. In some aspects, the outer knob includes a transverse wall at the interface between the proximal and distal lumen portions of the knob lumen, the transverse wall facing proximally into the proximal lumen portion. The longitudinal apertures of the outer knob may each include an opening defined in the transverse wall. The longitudinal apertures may extend distally from the openings along axes parallel to a longitudinal axis defined through the knob lumen.

The longitudinal apertures of the outer knob may include non-threaded inner walls and the screws may be thread-forming screws configured to form mating threads in the non-threaded inner walls of the longitudinal apertures.

The distal lumen portion of the knob lumen may include a ridge extending from an interior surface thereof, and the inner sleeve may include a cut-out defined in a distal end portion thereof configured to engage the ridge.

In aspects, the intermediate collar is disposed within a proximal lumen portion of the knob lumen, and the inner sleeve extends distally beyond the intermediate collar into the distal lumen portion of the knob lumen. In some aspects, the intermediate collar includes a body portion and a proximal collar extension extending proximally from the body portion, and the inner sleeve includes an outwardly-extending annular lip disposed at a proximal end portion thereof, the annular lip disposed within the proximal collar extension.

The intermediate collar may include proximal and distal annular protrusions extending outwardly from an exterior surface thereof that define bearing surfaces about which the outer knob rotates.

A handle assembly of a surgical instrument in accordance with aspects of the present disclosure includes a housing defining a body portion including a distal nose defining a distal opening therethrough, and a rotation knob assembly coupled to the distal nose of the housing. The rotation knob assembly includes an outer knob, an intermediate collar, an inner sleeve, a retaining clip, and screws. The outer knob defines a knob lumen extending longitudinally therethrough and longitudinal apertures disposed in radially spaced relation relative to a distal lumen portion of the knob lumen. The intermediate collar is disposed within the knob lumen and defines a collar lumen extending longitudinally therethrough. The inner sleeve is disposed within the knob lumen and extends through the collar lumen. The inner sleeve includes an annular groove defined in an exterior surface thereof. The retaining clip includes a curved body and prongs disposed at opposed ends of the curved body. The curved body is disposed within the annular groove of the inner sleeve and the prongs are aligned with the longitudinal apertures of the outer knob. The screws extend through the prongs of the retaining clip and into the longitudinal apertures of the outer knob to secure the outer knob and the inner sleeve with one another such that the outer knob and the inner sleeve are together rotatable relative to the intermediate collar.

In aspects, the knob lumen of the outer knob of the rotation knob assembly includes a proximal lumen portion having a diameter greater than a diameter of the distal lumen portion of the knob lumen. In some aspects, the outer knob includes a transverse wall at the interface between the proximal and distal lumen portions of the knob lumen, the transverse wall facing proximally into the proximal lumen portion. The longitudinal apertures of the outer knob may each include an opening defined in the transverse wall, the longitudinal apertures extending distally from the openings along axes parallel to a longitudinal axis defined through the knob lumen.

The distal lumen portion of the knob lumen may include a ridge extending from an interior surface thereof, and the inner sleeve may include a cut-out defined in a distal end portion thereof configured to engage the ridge.

In aspects, the intermediate collar is disposed within a proximal lumen portion of the knob lumen, and the inner sleeve extends distally beyond the intermediate collar into the distal lumen portion of the knob lumen. In some aspects, the intermediate collar includes a body portion and a proximal collar extension extending proximally from the body portion, and the inner sleeve includes an outwardly-extending annular lip disposed at a proximal end portion thereof, the annular lip disposed within the proximal collar extension.

The nose portion of the housing may include an annular recess defined in an interior surface thereof surrounding the distal opening, and the proximal collar extension of the intermediate collar may be disposed within the annular recess to fixedly engage the intermediate collar with the housing.

A surgical instrument in accordance with aspects of the present disclosure includes a handle assembly and an elongated assembly. The handle assembly includes a housing defining a body portion including a distal nose defining a distal opening therethrough, and a rotation knob assembly coupled to the distal nose of the housing. The rotation knob assembly includes an outer knob, an intermediate collar, an inner sleeve, a retaining clip, and screws. The outer knob defines a knob lumen extending longitudinally therethrough and longitudinal apertures disposed in radially spaced relation relative to a distal lumen portion of the knob lumen. The intermediate collar is disposed within the knob lumen and defines a collar lumen extending longitudinally therethrough. The inner sleeve is disposed within the knob lumen and extends through the collar lumen. The inner sleeve includes an annular groove defined in an exterior surface thereof. The retaining clip includes a curved body and prongs disposed at opposed ends of the curved body. The curved body is disposed within the annular groove of the inner sleeve and the prongs are aligned with the longitudinal apertures of the outer knob. The screws extend through the prongs of the retaining clip and into the longitudinal apertures of the outer knob to secure the outer knob and the inner sleeve with one another such that the outer knob and the inner sleeve are together rotatable relative to the intermediate collar. The elongated assembly is releasably coupled to the rotation knob assembly of the handle assembly. The elongated assembly supports an end effector assembly at a distal end portion thereof.

The distal lumen portion of the outer knob may include grooves defined in an interior surface thereof configured to receive corresponding indexing protrusions of a proximal hub of the elongated assembly to rotationally fix the elongated assembly to the outer knob.

The housing of the handle assembly may include a latch assembly including a latch lever having an engagement tooth configured to releasably engage an annular channel defined in a proximal hub of the elongated assembly.

BRIEF DESCRIPTION OF THE DRAWINGS

Aspects and features of the present disclosure are described in detail with reference to the drawing figures wherein like reference numerals identify similar or identical structural elements and:

FIG. 4 is a longitudinal, cross-sectional view of a portion of the handle assembly of the surgical clip applier of FIG. 1, including the elongated assembly of FIG. 1 engaged therewith;

FIG. 5 is a transverse, cross-sectional view taken across section line 5-5 of FIG. 4;

FIG. 6 is a rear, perspective view of a rotation knob assembly of the handle assembly of the surgical clip applier of FIG. 1;

FIG. 7 is an exploded, perspective view of the rotation knob assembly of FIG. 6.

DETAILED DESCRIPTION

The present disclosure provides rotation knob assemblies for surgical instruments. Although the rotation knob assemblies are discussed herein below as incorporated into surgical clip appliers, the rotation knob assemblies of the present disclosure may be incorporated into any suitable surgical instrument. Throughout this description, as is traditional when referring to relative positioning of a surgical instrument, the term "proximal" refers to a portion of the surgical instrument, or a component thereof, which is closer to a user, and the term "distal" refers to a portion of the surgical instrument or a component thereof which is further away from the user.

Turning to FIGS. 1-5, a surgical clip applier in accordance with aspects of the present disclosure is shown generally as clip applier 10. The clip applier 10 includes a handle assembly 100 and a plurality of elongated assemblies 200, 300 selectively connectable to the handle assembly 100. The handle assembly 100 is configured to operate each of the plurality of elongated assemblies 200, 300 upon connection thereto, and may be configured as a sterilizable, reusable component such that the handle assembly 100 may be repeatedly used with different and/or additional elongated assemblies 200, 300 during the course of one or more surgical procedures. The elongated assemblies 200, 300 may be configured as single-use disposable components, limited-use disposable components, or reusable components, depending upon a particular purpose and/or the configuration of the particular elongated assembly. In either configuration, the need for multiple handle assemblies is obviated and, instead, a user (e.g., a surgeon) need only select an appropriate elongated assembly 200, 300 and connect that elongated assembly 200, 300 to the handle assembly 100 in preparation for use.

The clip applier 10 will only be described to the extent necessary to fully disclose aspects of the present disclosure. For a detailed description of the structure and function of exemplary clip appliers (e.g., handle and elongated assemblies, and components thereof) suitable for use with the rotation knob assemblies of the present disclosure, reference may be made to Intl. Patent Appl. Publication Nos. WO/2017/059587, filed on Oct. 10, 2015, WO/2018/035796, filed on Aug. 26, 2016, and WO/2017/124217, filed on Jan. 18, 2016, and U.S. Patent Appl. Publication No. 2017-0128071, filed on Nov. 2, 2016, the entire contents of each of which are hereby incorporated herein by reference. It should be appreciated that the principles of the present disclosure are equally applicable to surgical instruments having other configurations such as, for example, powered surgical devices and/or different end effector assemblies (e.g., staplers, graspers, scissors, knives, etc.).

Figure 2:
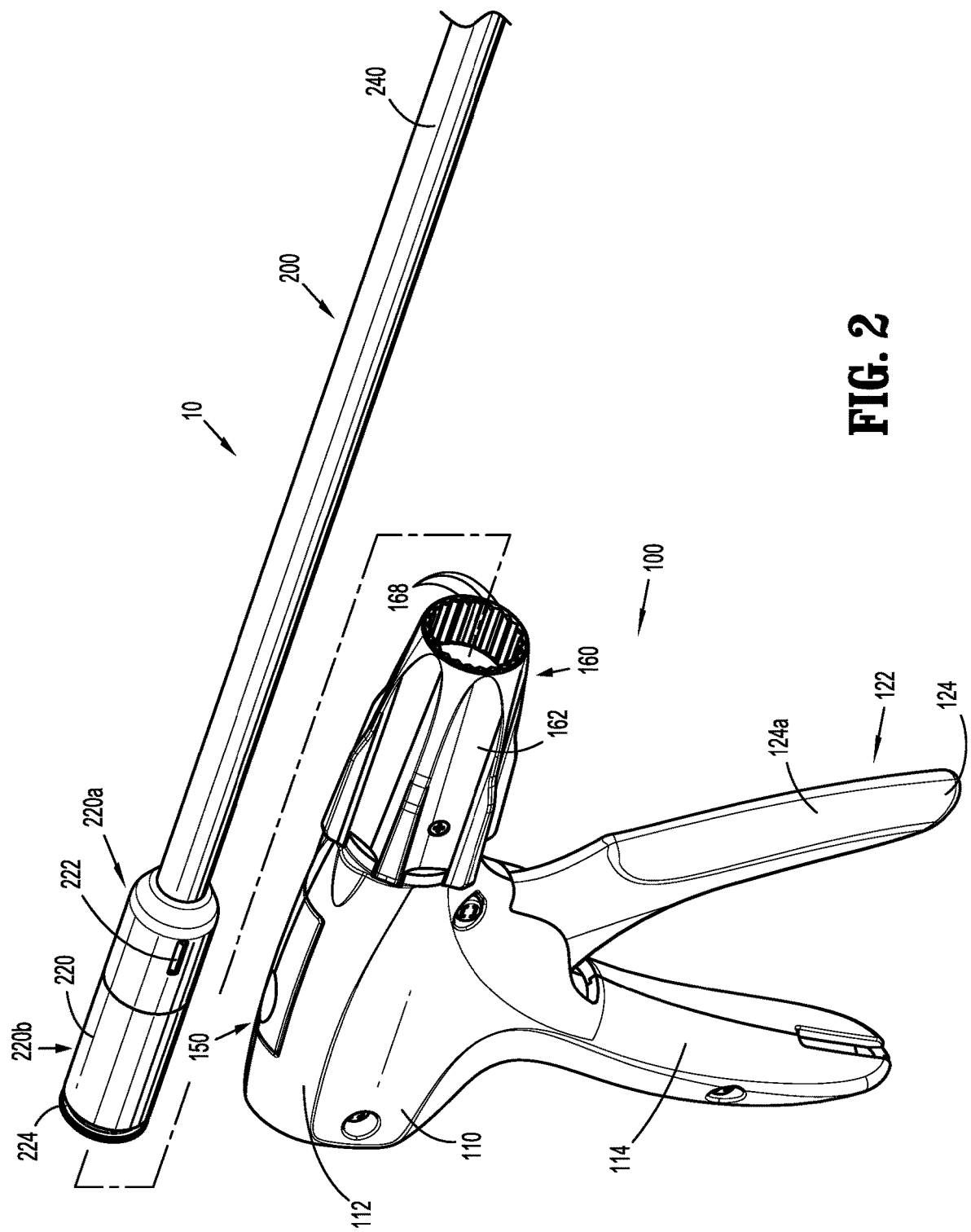
FIG. 2 is front, perspective view of the surgical clip applier shown in FIG. 1, with the elongated assembly removed from the handle assembly.
Figure 3A:
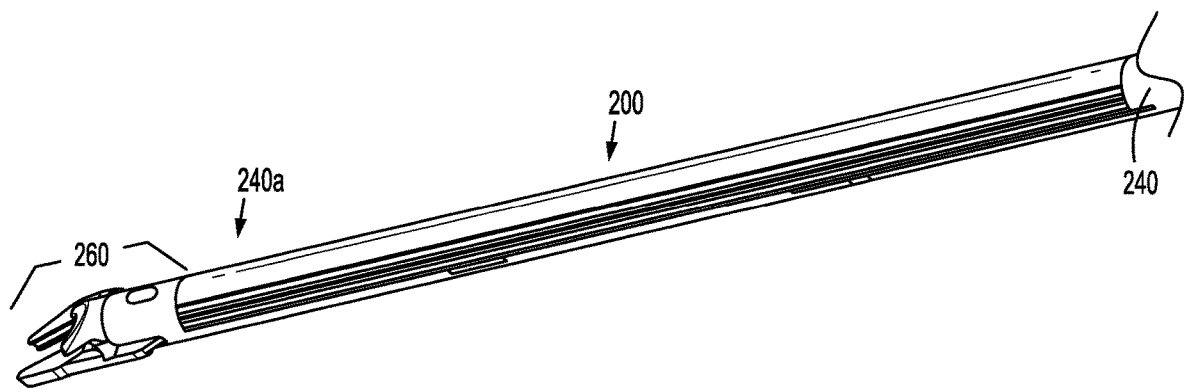
FIG. 3A is a side, perspective view of a distal end portion of the elongated assembly of FIGS. 1 and 2, configured to apply surgical clips.
Figure 3B:
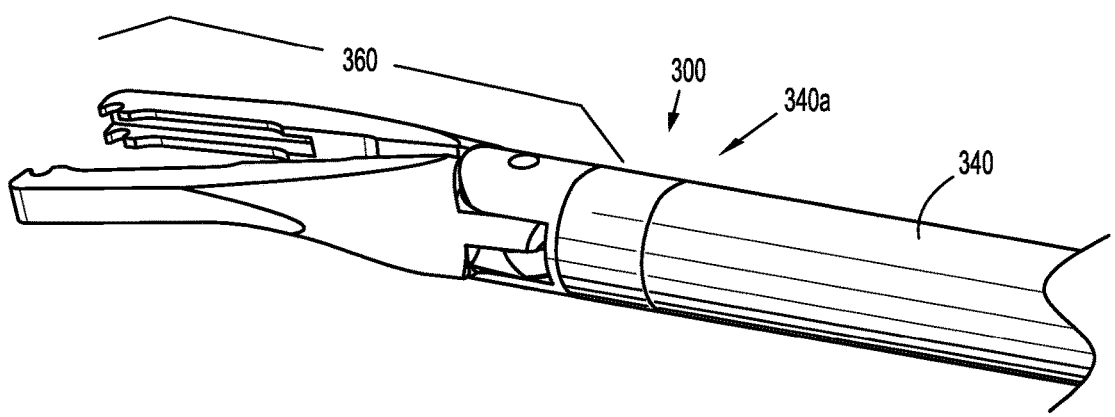
FIG. 3B is a side, perspective view of a distal end portion of another elongated assembly configured for use with the handle assembly of FIG. 1, configured to apply surgical clips or fasteners.

The handle assembly 100 is configured for use with different elongated assemblies such as, for example, elongated assembly 200 (FIGS. 1-3A) and elongated assembly 300 (FIG. 3B). The handle assembly 100, more specifically, is configured for both ratcheting use, e.g., in connection with elongated assembly 200 (FIGS. 1-3A), and non-ratcheting use, e.g., in connection with elongated assembly 300 (FIG. 3B).

As shown in FIGS. 1-3A, the elongated assembly 200 generally includes a proximal hub 220, an elongated shaft 240 extending distally from the proximal hub 220, an end effector assembly 260 disposed towards a distal end portion 240a of the elongated shaft 240, and an inner drive assembly (not shown) operably coupled between the handle assembly 100 and the end effector assembly 260 when the elongated assembly 200 is engaged with the handle assembly 100 to enable the sequential firing of at least one surgical clip (not shown) from the end effector assembly 260 about tissue. The end effector assembly 260 may be integrally formed with the elongated assembly 200 or may be a separate component releasably secured to the elongated assembly 200. The end effector assembly 260 of the elongated assembly 200 may be configured to fire surgical clips similar to those shown and described in U.S. Pat. Nos. 7,819,886 or 7,905,890, the entire contents of each of which are hereby incorporated herein by reference.

The proximal hub 220 of the elongated assembly 200 defines a plurality of indexing protrusions 222 annularly disposed thereabout towards a distal end portion 220a thereof, an annular channel 224 defined therein towards a proximal end portion 220b thereof, and a proximal tube extension 226 (FIG. 4) extending proximally from the proximal hub 220. The indexing protrusions 222 are configured for slidable receipt within longitudinally-extending grooves 168 defined within an outer knob 162 of a rotation knob assembly 160 of the clip applier 10 to rotationally fix the proximal hub 220 of the elongated assembly 200 relative to the rotation knob assembly 160 upon insertion of the proximal hub 220 therethrough (see also FIGS. 4 and 5). As such, in use, rotation of the outer knob 162 of the rotation knob assembly 160 relative to a housing 110 of the handle assembly 100 effects corresponding rotation of the elongated assembly 200 relative to the housing 110 of the handle assembly 100.

Figure 1:
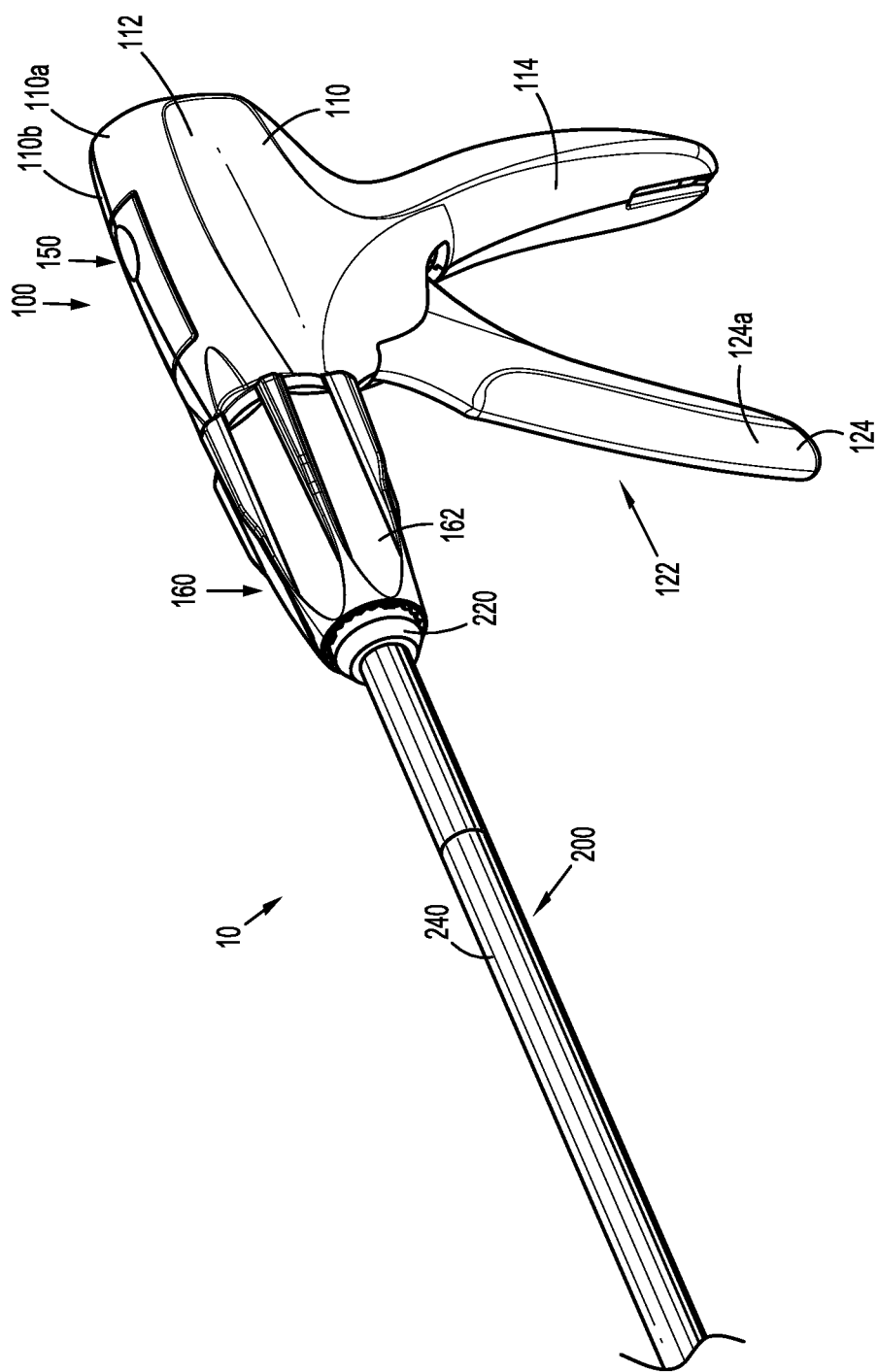
FIG. 1 is a front, perspective view of a surgical clip applier in accordance with aspects of the present disclosure including a handle assembly and an elongated assembly engaged therewith.

As shown in FIG. 3B, in conjunction with FIGS. 1 and 2, the elongated assembly 300 generally includes a proximal hub (not shown), an elongated shaft 340 extending distally from the proximal hub, an end effector assembly 360 disposed towards a distal end portion 340a of the elongated shaft 340, and an inner drive assembly (not shown) operably coupled between the handle assembly 100 and the end effector assembly 360 when the elongated assembly 300 is engaged with the handle assembly 100 to enable grasping and/or manipulation of tissue, retrieval of a surgical clip, and firing of a surgical clip about tissue. The end effector assembly 360 may be integrally formed with the elongated assembly 300 or may be a separate component releasably secured to the elongated assembly 300. The end effector assembly 360 of the elongated assembly 300 may be configured to fire surgical clips similar to those shown and described in U.S. Pat. No. 4,834,096, the entire contents of which are hereby incorporated herein by reference.

The proximal hub (not shown) of the elongated assembly 300 includes indexing protrusions and an annular channel similarly as described above with respect to the proximal hub 220 of the elongated assembly 200 and, in contrast to the proximal hub 220, does not include a proximal tube extension extending therefrom. The indexing protrusions rotationally fix the elongated assembly 300 relative to the rotation knob assembly 160 of the handle assembly 100 upon insertion of the proximal hub therethrough to enable rotation of the elongated assembly 300 relative to the housing 110 in response to rotation of the outer knob 162 of the rotation knob assembly 160 relative to the housing 110.

Although exemplary elongated assemblies 200, 300 configured for ratcheting and non-ratcheting use, respectively, are described above, it is contemplated that various other elongated assemblies for performing various different surgical tasks and/or having various different configurations suitable for ratcheting or non-ratcheting use may likewise be utilized with the handle assembly 100.

With continued reference to FIGS. 1, 2, and 4, the handle assembly 100 generally includes a housing 110, an actuation mechanism 120 including a trigger assembly 122 pivotably coupled to the housing 110 and a drive assembly 130 operably coupled to the trigger assembly 122, a ratchet mechanism 140 selectively operably associated with the drive assembly 130, a latch assembly 150 at least partially disposed within a cut-out defined within the housing 110 to enable manual manipulation thereof, and a rotation knob assembly 160 operable coupled to a nose 116 of the housing 110. The housing 110 supports and/or encloses the operating components of the handle assembly 100.

The housing 110 of handle assembly 100 may be formed from first and second housing halves 110a, 110b that cooperate to define a body portion 112 and a fixed handle portion 114 depending from the body portion 112. The body portion 112 of the housing 110 includes a distal nose 116 defining a distal opening 118a therethrough. A proximal end portion of a proximal hub of an elongated assembly, e.g., the proximal hub 220 of the elongated assembly 200 (FIGS. 1-3A) or the proximal hub (not shown) of the elongated assembly 300 (FIG. 3B), is configured to extend at least partially through the distal opening 118a of the distal nose 116 of the housing 110 when the elongated assembly 200, 300 is engaged with the handle assembly 100.

The distal nose 116 of the body portion 112 of the housing 110 further includes an annular recess 118b defined on an interior surface thereof surrounding the distal opening 118a. The annular recess 118b is configured to receive a proximal flange 184 of an intermediate collar 180 of the rotation knob assembly 160 to fixedly engage the intermediate collar 180 with the distal nose 116 of the body portion 112 of the housing 110, thereby rotatably engaging an outer knob 162 and an inner sleeve 170 of the rotation knob assembly 160 with the body portion 112 of the housing 110. To this end, the annular recess 118b and/or the proximal flange 184 may include keying features or other suitable features or materials (not shown) to facilitate rotationally-locked engagement therebetween.

The actuation mechanism 120 of the handle assembly 100 is configured to enable selective firing of one or more surgical clips (not shown) from an end effector assembly of an attached elongated assembly. The trigger assembly 122 of the actuation mechanism 120 includes a trigger 124, a linkage 126, and a biasing member 128. The trigger 124 includes a grasping portion 124a, an intermediate pivot portion 124b, and a proximal extension 124c. The grasping portion 124a of the trigger 124 extends from the body portion 112 of the housing 110 in opposed relation relative to the fixed handle portion 114 and is configured to facilitate grasping and manipulation of the trigger assembly 122. The intermediate pivot portion 124b of the trigger 124 is at least partially disposed within the housing 110 and defines a pivot aperture (not explicitly shown) configured to receive a pivot post 115 that extends transversely within the body portion 112 of the housing 110 so as to enable pivoting of the trigger 124 about the pivot post 115 and relative to the housing 110, e.g., between an un-actuated position, wherein the grasping portion 124a of the trigger 124 is spaced-apart relative to the fixed handle portion 114, and an actuated position, wherein the grasping portion 124a of the trigger 124 is approximated relative to the fixed handle portion 114.

The proximal extension 124c of the trigger 124 is disposed on an opposite side of the intermediate pivot portion 124b and, thus, the pivot post 115, as compared to the grasping portion 124a of the trigger 124. As such, pivoting of the grasping portion 124a to rotate in one direction, e.g., proximally towards the fixed handle portion 114, pivots the proximal extension 124c to rotate in the opposite direction, e.g., distally. The proximal extension 124c of the trigger 124 is pivotably coupled to a first or proximal end 126a of the linkage 126. The biasing member 128 is secured to and extends between the proximal extension 124c of the trigger 124 and a support (not shown) disposed within the fixed handle portion 114 of the housing 110. Pivoting of the grasping portion 124a towards the actuated position elongates the biasing member 128 storing energy therein such that, upon release of the grasping portion 124a, the grasping portion 124a is returned towards the un-actuated position under the bias of the biasing member 128. Although illustrated as an extension coil spring, the biasing member 128 may define any suitable configuration for biasing the grasping portion 124a of the trigger 124 towards the un-actuated position.

The drive assembly 130 includes a drive bar 132 having a proximal extension 132a and a ratchet rack 134. The drive bar 132 extends in a generally longitudinal direction and is longitudinally translatable relative to the housing 110. The proximal extension 132a of the drive bar 132 is pivotably coupled to a second or distal end 126b of the linkage 126 and, as noted above, the linkage 126 is coupled at its proximal end 126a to the proximal extension 124c of the trigger 124. As a result of this configuration, pivoting of the grasping portion 124a of the trigger 124 towards the actuated position urges the proximal extension 124c of the trigger 124 distally which, in turn, urges the linkage 126 distally to, in turn, urge the drive bar 132 distally.

The drive bar 132 is slidable through the body portion 112 of the housing 110, in response to actuation of the trigger 124, to urge a distal end portion 132b of the drive bar 132 into contact with a proximal actuator of an inner drive assembly (not shown) of an elongated assembly, e.g., elongated assembly 200 (FIGS. 1-3A) or elongated assembly 300 (FIG. 3B), engaged with the handle assembly 100 to fire a surgical clip supported at an end effector assembly of the elongated assembly. The drive bar 132, more specifically, is slidable from an un-actuated, proximal position, corresponding to the un-actuated position of the grasping portion 124a of the trigger 124, to an actuated, distal position, corresponding to the actuated position of the grasping portion 124a of the trigger 124, in order to urge the proximal actuator of the inner drive assembly (not shown) of the elongated assembly distally to fire a surgical clip supported at the end effector assembly of the elongated assembly.

The ratchet rack 134 of the drive assembly 130 extends along at least a portion of a surface (e.g., an underside surface) of the drive bar 132. The ratchet rack 134 is configured to selectively interface with the ratchet mechanism 140 to enable advancement of the drive bar 132 in either a ratcheting condition or a non-ratcheting condition.

The ratchet mechanism 140 enables ratcheting advancement of the drive assembly 130 when an elongated assembly configured for ratcheting actuation, e.g., elongated assembly 200, is connected to the handle assembly 100. The ratchet mechanism 140 includes a pawl assembly 141 and a cam assembly 145. The pawl assembly 141 includes a ratchet pawl 142 pivotably disposed about a pawl pin 144, which extends transversely within the housing 110. The ratchet pawl 142 is also transversely slidable about the pawl pin 144 and relative to the drive assembly 130. A transverse biasing member (not shown) biases the ratchet pawl 142 towards an off-set position relative to the ratchet rack 134 of the drive assembly 130, corresponding to the non-ratcheting condition of the ratchet mechanism 140 in which the ratchet pawl 142 is inhibited from operably engaging the ratchet rack 134 upon distal advancement of the drive bar 132. The ratchet pawl 142 is transversely slidable, against the bias, from the off-set position to an aligned position relative to the ratchet rack 132 of the drive assembly 130, corresponding to the ratcheting condition of the ratchet mechanism 140 in which ratchet pawl 142 is positioned to operably engage the ratchet rack 134 upon distal advancement of the drive bar 132.

The cam assembly 145 includes a cam arm 146 disposed about the pawl pin 144 adjacent the ratchet pawl 142. The cam arm 146 is slidable received, in fixed rotational orientation, within a slot 148a of a cam slider 148. A pawl biasing member 147 is coupled to and disposed between a free end of the cam arm 146 and the ratchet pawl 142 so as to bias the ratchet pawl 142 towards an operable orientation relative to the ratchet rack 134 of the drive assembly 130. The pawl biasing member 147 may be configured as a coil extension spring, although other configurations are also contemplated.

The cam slider 148 is slidable received within a longitudinally-extending guide track 119 defined within the housing 110 to confine the cam slider 148 to longitudinal translation within and relative to the housing 110. The cam slider 148 and the cam arm 146 are configured and dimensioned such that proximal translation of the cam slider 148 relative to the cam arm 146 urges the cam arm 146 transversely along the pawl pin 144 towards the ratchet pawl 142 to similarly urge the ratchet pawl 142 transversely along the pawl pin 144 from the off-set position towards the aligned position against the bias of the transverse biasing member (not shown). Return of the cam slider 148 distally permits the ratchet pawl 142 and, thus, the cam arm 146, to return transversely towards the off-set position under the bias of the transverse biasing member.

A cam slider biasing member 149 is retained within the guide track 119 of the housing 100, positioned to bias the cam slider 148 distally, and may be configured as a coil compression spring (although other configurations are also contemplated). As such, in the absence of other influence, the cam slider 148 is biased towards a distal-most position and, accordingly, the ratchet pawl 142 is biased towards the off-set position. In response to engagement of an elongated assembly for ratcheting use, e.g., elongated assembly 200, with the handle assembly 100, as shown in FIG. 4, the proximal tube extension 226 of the proximal hub 220 of the elongated assembly 200 contacts and urges the cam slider 148 of the ratchet mechanism 140 proximally to move the ratchet pawl 142 from the off-set position to the aligned position thereby engaging the ratcheting condition of the handle assembly 100.

The latch assembly 150 is configured to facilitate releasable locking engagement of an elongate assembly relative to the housing 110 of the handle assembly 100. The latch assembly 150 includes a latch lever 152, a pivot pin 154, and a biasing member 156. The latch lever 152 defines a distal engagement section 152a, an intermediate section 152b, and a proximal manipulatable section 152c. The distal engagement section 152a of the latch lever 152 includes an engagement tooth 158 extending therefrom. The engagement tooth 158 is configured to engage an elongated assembly inserted into the handle assembly 100. With respect elongated assembly 200, for example, upon insertion of the proximal hub 220 of the elongated assembly 200 into the handle assembly 100, the engagement tooth 158 is configured to cam over the proximal end portion 220b of the proximal hub 220 and into engagement within the annular channel 224 to thereby lock the elongated assembly 200 in engagement with the handle assembly 100.

The pivot pin 154 of the latch assembly 150 pivotably couples the intermediate section 152b of the lever latch 152 with the housing 110 such that urging of the proximal manipulation section 152c of lever latch 152 in a first direction into the housing 110, urges the distal engagement section 152a of the lever latch 152 in a second, opposite direction out of engagement with the annular channel 224 of the proximal hub 220 of the elongated assembly 200. The biasing member 156 is configured as a torsion spring biasing the distal engagement section 152a of the lever latch 152 towards an engaged position. However, other suitable configurations of the biasing member 156 are also contemplated. The proximal manipulation section 152c of the lever latch 152 is selectively depressible, against the bias of the biasing member 156, to urge the distal engagement section 152a towards a disengaged position.

The rotation knob assembly 160 is configured to enable selective rotation of an attached elongated assembly relative to the housing 110. As discussed above, the rotation knob assembly 160 is coupled to the distal nose 116 of the body portion 112 of the housing 110 and is configured to receive a proximal hub of an elongated assembly, e.g., the proximal hub 220 of the elongated assembly 200, coupled to the handle assembly 100 in fixed rotational engagement therewith to enable the selective rotation of the elongated assembly 200 relative to the housing 110 upon rotation of the outer knob 162 of the rotation knob assembly 160 relative to the housing 110.

Figure 8:
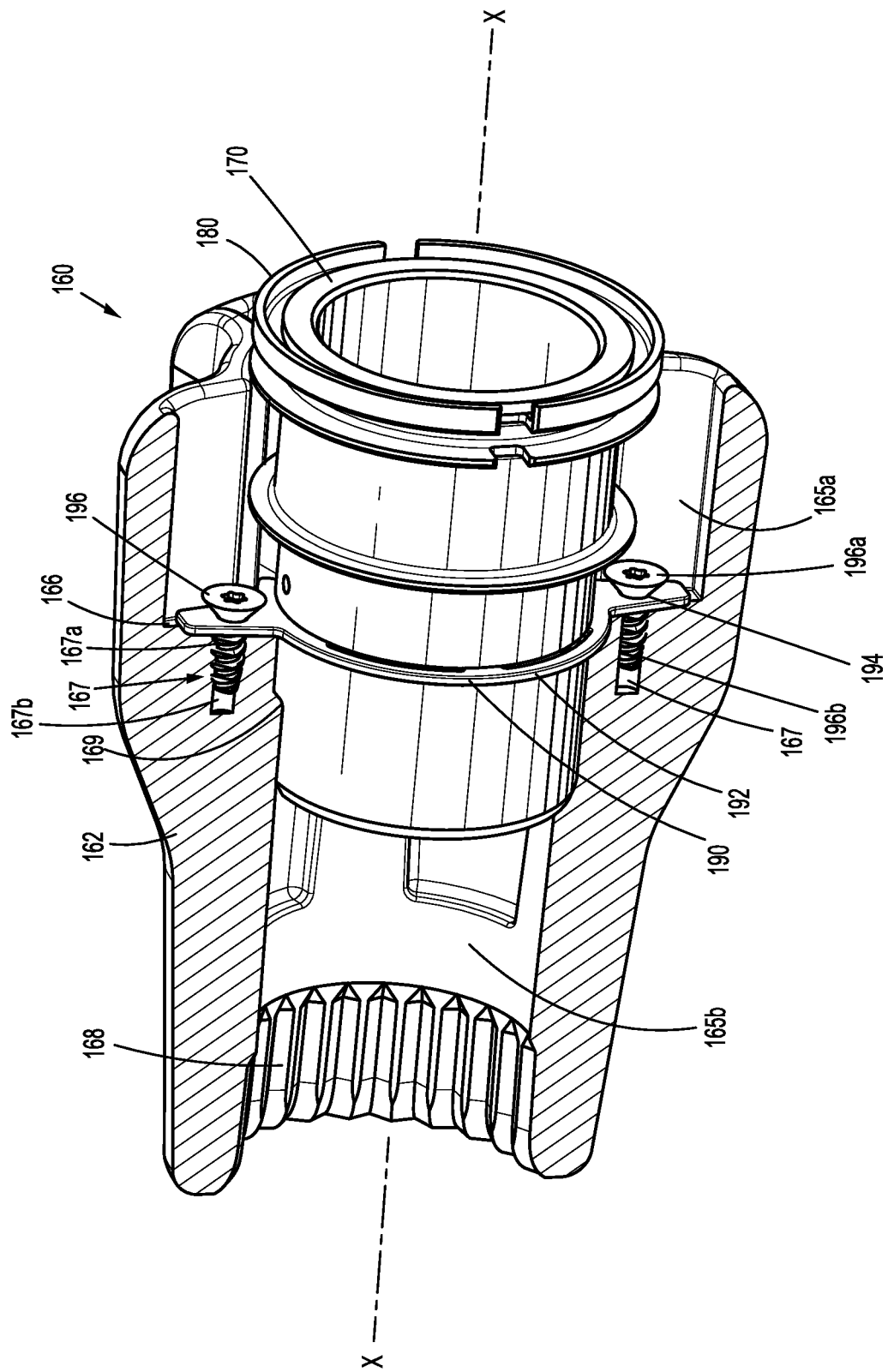
FIG. 8 is a longitudinal, partial cross-sectional view of the rotation knob assembly of FIG. 6.

Referring now to FIGS. 6-8, the rotation knob assembly 160 includes an outer knob 162, an inner sleeve 170, and intermediate collar 180. The rotation knob assembly 160 further includes a retaining clip 190 and screws 196. The outer knob 162 and the inner sleeve 170 are fixedly engaged to one another via the retaining clip 190 and the screws 196, and rotatable relative to the intermediate collar 180 which is radially disposed therebetween.

The outer knob 162 of the rotation knob assembly 160 may be formed from a polymeric material, e.g., a biocompatible, sterilizable plastic, or other suitable material, via molding or other suitable process. The outer knob 162 has a cone shaped-configuration tapering in diameter from a proximal portion 162a to a distal portion 162b thereof, although other suitable configurations are also contemplated. An exterior surface of the outer knob 162 is continuous and free of apertures (e.g., no screw holes), and includes a plurality of flutes 164 arranged radially thereabout to facilitate grasping or gripping of the outer knob 162 at any rotational orientation to enable rotation thereof.

With specific reference to FIG. 8, outer knob 162 of the rotation knob assembly 160 further includes a knob lumen 165 extending longitudinally therethrough along a longitudinal axis "X." The knob lumen 165 includes a proximal lumen portion 165a and a distal lumen portion 165b defined by an interior surface of the outer knob 162. The proximal lumen portion 165a of the knob lumen 165 has a diameter larger than a diameter of the distal lumen portion 165b of the knob lumen 165. A transverse wall or step 166 is disposed at the interface between the proximal and distal lumen portions 165a, 165b of the knob lumen 165, and faces proximally into the proximal lumen portion 165a.

Longitudinal apertures 167, e.g., a pair of opposed longitudinal apertures, are defined in the outer knob 162 along axes parallel to the longitudinal axis "X" defined through the knob lumen 165. The longitudinal apertures 167 each include an opening 167a defined in the transverse wall 166 that is in communication with the proximal lumen portion 165a of the knob lumen 165 and extends distally and linearly therefrom within the outer knob 162. Each of the longitudinal apertures 167 includes a non-threaded or smooth inner wall 167b extending along the entire length thereof configured to receive one of the screws 196 therein.

The distal lumen portion 165b of the knob lumen 165 includes grooves 168 arranged annularly in the interior surface of the outer knob 162 and disposed towards the distal end thereof which, as noted above, enable fixed rotational engagement of the proximal hub 220 of the elongated assembly 200 relative to the outer knob 162 of the rotation knob assembly 160 upon insertion of the proximal hub 220 therethrough (see FIGS. 2, 4, and 5). The distal lumen portion 165b of the knob lumen 165 further includes at least one ridge or bump 169 extending from the interior surface of the outer knob 162 and disposed towards the proximal end thereof which is configured to engage and be received within a cutout 173 defined in the inner sleeve 170.

With reference back to FIGS. 6-8, the inner sleeve 170 of the rotation knob assembly 160 may be formed from a metal, e.g., stainless steel, or other suitable material. The inner sleeve 170 has a cylindrical configuration including a sleeve lumen 171 extending longitudinally therethrough. The inner sleeve 170 further includes an outwardly-extending annular lip 172 disposed at a proximal end portion 170a of the inner sleeve 170, at least one notch or cut-out 173 defined in a distal end portion 170b of the inner sleeve 170, and an annular groove or channel 175 defined within an exterior surface of the inner sleeve 170 about an intermediate portion 170c of the inner sleeve 170 disposed between the proximal and distal end portions 170a, 170b.

The intermediate collar 180 of the rotation knob assembly 160 may be formed from a metal, e.g., stainless steel, or other suitable material. The intermediate collar 180 includes a body portion 182 and a proximal collar extension or flange 184 extending proximally and radially outwardly from the body portion 182. The intermediate collar 180 has a cylindrical configuration including a collar lumen 181 extending longitudinally therethrough. The intermediate collar 180 is configured to receive the inner sleeve 170 therethrough so that a bearing fit is established and an interior surface of the body portion 182 of the intermediate collar 180 that defines the collar lumen 181 provides a surface for the inner sleeve 170 to move (e.g., rotate). The diameter of the portion of the collar lumen 181 disposed within the proximal flange 184 is larger than the diameter of the portion of the lumen 181 disposed within the body portion 182 to receive the annular lip 172 of the inner sleeve 170 therein and prevent proximal longitudinal movement of the intermediate collar 180 relative to the inner sleeve 170.

The intermediate collar 180 further includes a proximal annular protrusion 186 extending outwardly from an exterior surface of the body portion 182 at a proximal end portion 182a of the body portion 182 in spaced longitudinal relation relative to the proximal flange 184, and a distal annular protrusion 188 extending outwardly from an exterior surface of the body portion 182 at a distal end portion 182b of the body portion 182.

As noted above, the intermediate collar 180 is radially disposed between the outer knob 162 and the inner sleeve 170. More specifically, the inner sleeve 170 is positioned within the intermediate collar 180 and the intermediate collar 180 is positioned within the proximal lumen portion 165a of the knob lumen 165 of the outer knob 162. The intermediate collar 180 defines a length less than a length of the inner sleeve 170 such that such that inner sleeve 170 extends distally beyond the intermediate collar 180 and into the distal lumen portion 165b of the knob lumen 165 of the outer knob 162.

With reference again to FIG. 4, in conjunction with FIGS. 6-8, the proximal flange 184 of the intermediate collar 180, as noted above, is configured for receipt within the annular recess 118b of the distal nose 116 of the body portion 112 of the housing 110, e.g., upon engagement of the first and second housing halves 110a, 110b (FIG. 1) forming the housing 110 with one another, thereby engaging the intermediate collar 180 with the body portion 112 of the housing 110 and, thus, coupling the outer knob 162 of the rotation knob assembly 160 about the distal nose 116 of the body portion 112 of the housing 110. The proximal flange 184 of the intermediate collar 180 defines openings 185 for receiving tabs (not shown) extending from the distal nose 116 of the housing 110 for rotationally locking the intermediate collar 180 relative to the housing 110.

While the intermediate collar 180 is longitudinally and rotationally fixed relative to the housing 110, the outer knob 162 and the inner sleeve 170 are fixed to one another and together rotatable about and relative to the intermediate collar 180 and, thus, relative to the housing 110, e.g., to enable rotation of the elongated assembly 200 relative to the housing 110. The proximal and distal annular protrusions 186, 188 of the intermediate collar 180 define bearing surfaces about which the outer knob 162 rotates, facilitating smooth rotation of the outer knob 162 relative to intermediate collar 180.

The retaining clip 190 and the screws 196 fix the outer knob 162 and the inner sleeve 170 to one another to enable the outer knob 162 and the inner sleeve 170 to rotate together relative to the intermediate collar 180 and the housing 110. The retaining clip 190 includes curved body 192 having a substantially semi-annular or semi-circular configuration (e.g., a c-shaped or u-shaped cross-section) including first and second brackets or prongs 194 extending from opposed ends thereof. The curved body 192 is configured for positioning within the annular groove 175 of the inner sleeve 170 to mount the retaining clip 190 to the inner sleeve 170, and the prongs 194 are configured for positioning against the transverse wall 166 disposed within the knob lumen 165 of the outer knob 162. Each of the prongs defines an opening 195 therethrough that is configured to align with the respective opening 167a of the longitudinal apertures 167 of the outer knob 162. One or more intermediate prongs (not shown) may extend from the curved body 192 of the retaining clip 190 (e.g., the retaining clip 190 may have an e-shaped cross-section) to engage and retain the curved body 192 to the inner sleeve 170.

The screws 196 are configured to secure the retaining clip 190 within the outer knob 162 to thereby retain the inner sleeve 170 and the outer knob 162 in fixed engagement with one another. Each of the screws 196 includes a head 196a and a threaded shank 196b extending from the head 196a. The threaded shanks 196b of the screws 196 are configured as thread-forming or thread-cutting screws to form mating threads in the non-threaded inner wall 167b of the longitudinal apertures 167 of the outer knob 162 to retain the screws 196 therein and minimize loosening of the screws 196. Alternatively, the threaded shanks 196b of the screws 196 may be configured for threaded engagement with pre-formed threads of the longitudinal apertures 167 of the outer knob 162.

The screws 196 are received within the longitudinal apertures 167 of the outer knob 162 and are oriented such that the threaded shanks 196b are engaged with the respective opening 195 of the retaining clip 190 and the longitudinal apertures 167 of the outer knob 162, and the heads 196a of the screws 196 are positioned or seated against the respective prong 194 of the retaining clip 190.

The rotation knob assembly 160 is assembled by sliding the inner sleeve 170 through the lumen 181 of the intermediate collar 180 until the body portion 182 of the intermediate collar 180 is disposed over the proximal end portion 170a of the inner sleeve 170 and the proximal flange 184 is coaxial with the annular lip 172. The curved body 192 of the retaining clip 190 is then snapped into the annular groove 175 of the inner sleeve 170. This assembly is loaded into the outer knob 162 until the cut-out 173 of the inner sleeve 170 engages the ridge 169 of the outer knob 162 to fix the inner sleeve 170 to the outer knob 162, and the prongs 194 of the retaining clip 190 abut the transverse wall 166 of the outer knob 162 with the openings 195 of the retaining clip 190 aligned with the longitudinal apertures 167 of the outer knob 162. The screws 196 are then driven through the openings 195 of the retaining clip 190 and into the longitudinal apertures 167 of the outer knob 162 until the heads 196a of the screws 196 are seated against the prongs 194 of the retaining clip 190 to affix the retaining clip 190 and thus, the inner sleeve 170, to the outer knob 162. Once the screws 196 are properly seated, the rotation knob assembly 160 is locked together. The assembled rotation knob assembly 160 may then be secured to the housing 110 of the handle assembly 100 by the intermediate collar 180, as described above.

Referring generally to FIGS. 1-8, a method of inserting and engaging an elongated assembly, e.g., elongated assembly 200, with the handle assembly 100 and use of the same are described in accordance with aspects of the present disclosure. In order to engage the elongated assembly 200 with the handle assembly 100, the proximal hub 220 of the elongated assembly 200 is inserted into the knob lumen 165 of the outer knob 162 and advanced proximally into the sleeve lumen 171 of the inner sleeve 170 and into the distal nose 116 of the housing 110. Upon insertion of the proximal hub 220 through the rotation knob assembly 160, the indexing protrusions 222 of the proximal hub 220 are slidably received within the grooves 168 of the outer knob 172 to rotationally fix the proximal hub 220 relative to the outer knob 172. As the proximal hub 220 enters the housing 110, the proximal hub 220 receives the distal end portion 132*b* of the drive bar 132 of the drive assembly 130, the engagement tooth 158 of the latch assembly 150 cams over the proximal end portion 220*b* of the proximal hub 220 and into engagement therewith to thereby rotatably engage the proximal hub 220 relative to the housing 110, and the proximal extension tube 226 of the proximal hub 220 is translated into contact with the cam slider 148 of the ratchet mechanism 140 for ratcheting use of the drive assembly 130.

With the elongated assembly 200 engaged with the handle assembly 100, the handle assembly 100 may be manipulated and/or the outer knob 162 of the rotation knob assembly 160 may be rotated to position the end effector assembly 260 of the elongated assembly 200 about tissue to be treated. Once the end effector assembly 260 is positioned as desired, the trigger 124 of the handle assembly 100 is pivoted towards the fixed handle portion 114 of the housing 110 to urge the linkage 126 distally which, in turn, urges the drive bar 132 distally through the housing 110 to drive the proximal actuator of the inner drive assembly (not shown) of the elongated assembly 200 distally through the elongated assembly 200 to fire and form a surgical clip from the end effector assembly 260 about tissue. The above may be repeated to fire and form several surgical clips about tissue, as necessary.

In order to disengage the elongated assembly 200 from the handle assembly 100, e.g., for cleaning and/or sterilization, or to replace the elongated assembly 200 with another elongated assembly, the lever latch 152 of the latch assembly 150 is depressed inwardly into the housing 110 to disengage the proximal hub 220 of the elongated assembly 200, thus enabling the proximal hub 220 to be withdrawn distally from the housing 110 and the rotation knob assembly 170.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A rotation knob assembly for a surgical instrument, the rotation knob assembly comprising:
   an outer knob defining a knob lumen extending longitudinally therethrough and longitudinal apertures disposed in radially spaced relation relative to a distal lumen portion of the knob lumen;
   an intermediate collar disposed within the knob lumen, the intermediate collar defining a collar lumen extending longitudinally therethrough;
   an inner sleeve disposed within the knob lumen and extending through the collar lumen of the intermediate collar, the inner sleeve including an annular groove defined in an exterior surface thereof;
   a retaining clip including a curved body and prongs disposed at opposed ends of the curved body, the curved body disposed within the annular groove of the inner sleeve and the prongs aligned with the longitudinal apertures of the outer knob; and
   screws extending through the prongs of the retaining clip and into the longitudinal apertures of the outer knob to secure the outer knob and the inner sleeve with one another such that the outer knob and the inner sleeve are together rotatable relative to the intermediate collar.

2. The rotation knob assembly according to claim 1, wherein a proximal lumen portion of the knob lumen has a diameter greater than a diameter of the distal lumen portion of the knob lumen.

3. The rotation knob assembly according to claim 2, wherein the outer knob includes a transverse wall at an interface between the proximal and distal lumen portions of the knob lumen, the transverse wall facing proximally into the proximal lumen portion.

4. The rotation knob assembly according to claim 3, wherein the longitudinal apertures of the outer knob each includes an opening defined in the transverse wall, the longitudinal apertures extending distally from the openings along axes parallel to a longitudinal axis defined through the knob lumen.

5. The rotation knob assembly according to claim 1, wherein the longitudinal apertures of the outer knob include non-threaded inner walls and the screws are thread-forming screws configured to form mating threads in the non-threaded inner walls of the longitudinal apertures.

6. The rotation knob assembly according to claim 1, wherein the distal lumen portion of the knob lumen includes a ridge extending from an interior surface thereof, and the inner sleeve includes a cut-out defined in a distal end portion thereof configured to engage the ridge.

7. The rotation knob assembly according to claim 1, wherein the intermediate collar is disposed within a proximal lumen portion of the knob lumen, and the inner sleeve extends distally beyond the intermediate collar into the distal lumen portion of the knob lumen.

8. The rotation knob assembly according to claim 7, wherein the intermediate collar includes a body portion and a proximal collar extension extending proximally from the body portion, and the inner sleeve includes an outwardly-extending annular lip disposed at a proximal end portion thereof, the annular lip disposed within the proximal collar extension.

9. The rotation knob assembly according to claim 1, wherein the intermediate collar includes proximal and distal annular protrusions extending outwardly from an exterior surface thereof, the proximal and distal annular protrusions defining bearing surfaces about which the outer knob rotates.

10. A handle assembly of a surgical instrument comprising:
    a housing defining a body portion including a distal nose defining a distal opening therethrough; and
    a rotation knob assembly coupled to the distal nose of the housing, the rotation knob assembly including:
       an outer knob defining a knob lumen extending longitudinally therethrough and longitudinal apertures disposed in radially spaced relation relative to a distal lumen portion of the knob lumen;
       an intermediate collar disposed within the knob lumen, the intermediate collar defining a collar lumen extending longitudinally therethrough;
       an inner sleeve disposed within the knob lumen and extending through the collar lumen of the intermediate collar, the inner sleeve including an annular groove defined in an exterior surface thereof;
       a retaining clip including a curved body and prongs disposed at opposed ends of the curved body, the curved body disposed within the annular groove of the inner sleeve and the prongs aligned with the longitudinal apertures of the outer knob; and screws extending through the prongs of the retaining clip and into the longitudinal apertures of the outer knob to secure the outer knob and the inner sleeve with one another such that the outer knob and the inner sleeve are together rotatable relative to the intermediate collar.

11. The handle assembly according to claim 10, wherein a proximal lumen portion of the knob lumen has a diameter greater than a diameter of the distal lumen portion of the knob lumen.

12. The handle assembly according to claim 11, wherein the outer knob includes a transverse wall at an interface between the proximal and distal lumen portions of the knob lumen, the transverse wall facing proximally into the proximal lumen portion.

13. The handle assembly according to claim 12, wherein the longitudinal apertures of the outer knob each includes an opening defined in the transverse wall, the longitudinal apertures extending distally from the openings along axes parallel to a longitudinal axis defined through the knob lumen.

14. The handle assembly according to claim 10, wherein the distal lumen portion of the knob lumen includes a ridge extending from an interior surface thereof, and the inner sleeve includes a cut-out defined in a distal end portion thereof configured to engage the ridge.

15. The handle assembly according to claim 10, wherein the intermediate collar is disposed within a proximal lumen portion of the knob lumen, and the inner sleeve extends distally beyond the intermediate collar into the distal lumen portion of the knob lumen.

16. The handle assembly according to claim 15, wherein the intermediate collar includes a body portion and a proximal collar extension extending proximally from the body portion, and the inner sleeve includes an outwardly-extending annular lip disposed at a proximal end portion thereof, the annular lip disposed within the proximal collar extension.

17. The handle assembly according to claim 16, wherein the distal nose of the housing includes an annular recess defined in an interior surface thereof surrounding the distal opening, the proximal collar extension of the intermediate collar disposed within the annular recess to fixedly engage the intermediate collar with the housing.

18. A surgical instrument comprising:
the handle assembly according to claim 10; and
an elongated assembly releasably coupled to the rotation knob assembly of the handle assembly, the elongated assembly supporting an end effector assembly at a distal end portion thereof.

19. The surgical instrument according to claim 18, wherein the distal lumen portion of the outer knob includes grooves defined in an interior surface thereof, the grooves configured to receive corresponding indexing protrusions of a proximal hub of the elongated assembly to rotationally fix the elongated assembly to the outer knob.

20. The surgical instrument according to claim 18, wherein the housing includes a latch assembly including a latch lever having an engagement tooth configured to releasably engage an annular channel defined in a proximal hub of the elongated assembly.

* * * * *